(12) United States Patent
Robilotto et al.

(10) Patent No.: US 8,784,409 B2
(45) Date of Patent: Jul. 22, 2014

(54) CRYOGENIC SYSTEM AND METHOD OF USE

(75) Inventors: Anthony Robilotto, Binghamton, NY (US); Kristi K. Snyder, Candor, NY (US); John G Baust, Candor, NY (US); John M. Buast, Owego, NY (US); Roy E. Cheeks, Harper's Ferry, WV (US)

(73) Assignee: Endocare, Inc., Austin, TX (US)

( * ) Notice: Subject to any disclaimer, the term of this patent is extended or adjusted under 35 U.S.C. 154(b) by 810 days.

(21) Appl. No.: 13/061,171

(22) PCT Filed: Nov. 2, 2009

(86) PCT No.: PCT/US2009/062928
§ 371 (c)(1),
(2), (4) Date: Feb. 28, 2011

(87) PCT Pub. No.: WO2010/028409
PCT Pub. Date: Mar. 11, 2010

(65) Prior Publication Data
US 2011/0152849 A1    Jun. 23, 2011

Related U.S. Application Data

(60) Provisional application No. 61/093,916, filed on Sep. 3, 2008, provisional application No. 61/098,244, filed on Sep. 19, 2008.

(51) Int. Cl.
*A61B 18/02* (2006.01)

(52) U.S. Cl.
USPC .......................................................... 606/22

(58) Field of Classification Search
USPC ................................................... 606/20–26
See application file for complete search history.

(56) References Cited

U.S. PATENT DOCUMENTS

| | | |
|---|---|---|
| 3,794,039 A | 2/1974 | Kollner et al. |
| 4,082,096 A | 4/1978 | Benson |
| 4,377,168 A | 3/1983 | Rzasa et al. |
| 4,829,785 A | 5/1989 | Hersey |
| 5,147,355 A | 9/1992 | Friedman et al. |
| 5,237,824 A | 8/1993 | Pawliszyn |

(Continued)

FOREIGN PATENT DOCUMENTS

WO    2010028409    3/2010

OTHER PUBLICATIONS

Bartlett, The Fundamentals of Heat Exchangers, Industrial Physicist (2006) 18-21.

(Continued)

*Primary Examiner* — Michael Peffley
*Assistant Examiner* — Daniel Fowler
(74) *Attorney, Agent, or Firm* — Pepper Hamilton LLP

(57) ABSTRACT

A cryogenic medical device for delivery of subcooled liquid cryogen to various configurations of cryoprobes is designed for the treatment of damaged, diseased, cancerous or other unwanted tissues. The device is a closed or semi-closed system in which the liquid cryogen is contained in both the supply and return stages. The device is capable of generating cryogen to a supercritical state and may be utilized in any rapid cooling systems. As designed, the device comprises a number of parts including a vacuum insulated outer dewar, submersible cryogen pump, baffled linear heat exchanger, multiple pressurization cartridges, a return chamber, and a series of valves to control the flow of the liquid cryogen interconnected with cryotreatment devices including cryoprobes and catheters. The cryogenic medical device promotes subcooling to the tips of various external cryogenic instrument configurations.

18 Claims, 14 Drawing Sheets

(56) References Cited

U.S. PATENT DOCUMENTS

| | | |
|---|---|---|
| 5,334,181 A | 8/1994 | Rubinsky et al. |
| 5,423,807 A | 6/1995 | Milder |
| 5,452,582 A | 9/1995 | Longsworth |
| 5,674,218 A | 10/1997 | Rubinsky et al. |
| 5,733,280 A | 3/1998 | Avitall |
| 5,746,736 A | 5/1998 | Tankovich |
| 5,758,505 A | 6/1998 | Dobak et al. |
| 5,916,212 A | 6/1999 | Baust et al. |
| 5,951,546 A | 9/1999 | Lorentzen |
| 6,096,032 A | 8/2000 | Rowland |
| 6,161,543 A | 12/2000 | Cox et al. |
| 6,171,301 B1 | 1/2001 | Nelson et al. |
| 6,306,129 B1 | 10/2001 | Little et al. |
| 6,468,268 B1 | 10/2002 | Abboud |
| 6,468,269 B1 | 10/2002 | Korpan et al. |
| 6,887,234 B2 | 5/2005 | Abboud et al. |
| 7,160,291 B2 | 1/2007 | Damasco et al. |
| 7,207,985 B2 | 4/2007 | Duong et al. |
| 7,303,554 B2 | 12/2007 | Lalonde et al. |
| 7,306,589 B2 | 12/2007 | Swanson |
| 7,416,548 B2 | 8/2008 | Baust et al. |
| 7,416,551 B2 | 8/2008 | Ad |
| 2001/0021847 A1 | 9/2001 | Abboud et al. |
| 2004/0215295 A1 | 10/2004 | Littrup et al. |
| 2005/0090814 A1 | 4/2005 | Lalonde et al. |
| 2005/0261671 A1 | 11/2005 | Baust et al. |
| 2005/0261753 A1 | 11/2005 | Littrup et al. |
| 2006/0079867 A1 | 4/2006 | Berzak et al. |
| 2006/0129142 A1 | 6/2006 | Reynolds |
| 2006/0235375 A1 | 10/2006 | Littrup et al. |
| 2007/0021741 A1 | 1/2007 | Abboud et al. |
| 2007/0233055 A1 | 10/2007 | Abboud et al. |
| 2007/0244474 A1 | 10/2007 | DeLonzor et al. |
| 2007/0277550 A1 | 12/2007 | Li et al. |
| 2008/0009845 A1 | 1/2008 | Duong et al. |
| 2008/0027422 A1 | 1/2008 | Vancelette et al. |
| 2008/0147056 A1 | 6/2008 | van der Weide et al. |
| 2008/0173028 A1 | 7/2008 | Littrup et al. |
| 2008/0255551 A1 | 10/2008 | DeLonzor |
| 2008/0300584 A1 | 12/2008 | Lentz et al. |
| 2009/0012510 A1 | 1/2009 | Bertolero et al. |
| 2009/0281533 A1 | 11/2009 | Ingle et al. |
| 2009/0318913 A1 | 12/2009 | Li |
| 2010/0057064 A1 | 3/2010 | Baust et al. |
| 2010/0057067 A1 | 3/2010 | Baust et al. |
| 2010/0241112 A1 | 9/2010 | Watson |
| 2011/0152849 A1 | 6/2011 | Baust et al. |

OTHER PUBLICATIONS

Office Action dated Feb. 20, 2013 received in related application U.S. Appl. No. 12/548,321.

Fladerer et al., "Homogenous nucleation and droplet growth in supersaturated argon vapor: The cryogenic nucleation pulse chamber", Journal of Chemical Physics (2006), vol. 124. 2006 American Institute of Physics. USA.

CRYOGENIC SYSTEM AND METHOD OF USE

RELATED APPLICATIONS

The present application claims priority to U.S. Non-provisional patent application Ser. No. 12/553,005 filed on Sep. 2, 2009, which claims priority to U.S. Provisional Patent Application Ser. No. 61/093,916 filed on Sep. 3, 2008, and titled Modular Pulsed Pressure Device for the Transport of Liquid Cryogen to a Cryoprobe, which is incorporated herein by reference; further claiming priority to U.S. Non-provisional patent application Ser. No. 12/562,301 filed on Sep. 18, 2009, which claims priority to U.S. Provisional Patent Application Ser. No. 61/098,244 filed on Sep. 19, 2008, and titled Nucleation Enhanced Surface Modification to Support Physical Vapor Deposition to Create a Vacuum, which is incorporated herein by reference.

FIELD OF THE INVENTION

The present invention relates generally to the medical technology field and, in particular, to a cryogenic system.

BACKGROUND OF THE INVENTION

Over a recent number of years, there has been a strong movement within the surgical community toward minimally invasive therapies. The main goals of the minimally invasive therapies include: 1) eradication of targeted tissue, 2) decreased hospitalization time, 3) limited postoperative morbidities, 4) shortened return interval to daily functions and work, and 5) reduced overall treatment cost. Cryotherapy is a minimally invasive method of treating a disease state through tissue freezing with thousands of patients now receiving the procedure annually. Currently, cryotherapy is used to treat numerous disease states including organ confined tumors such as prostate, kidney, liver, as well as cardiovascular disease, retinal detachment, pain management, and other illness/disease states.

Cryotherapy is an effective yet minimally invasive alternative to radical surgery and radiation therapy. The procedure is done under either general or epidural anesthesia. The procedure offers patients a quicker recovery and reduced severity of potential side effects. Without the expense associated with major surgery or an extended hospital stay, cryotherapy is a cost-effective treatment option.

The approaches utilized to date have focused on the delivery of liquid cryogen through the use of moderate to high pressure on the entire system or piston/bellows compression to drive fluid movement. At present, current systems utilizing liquid nitrogen operate at pressures between 14-480 psi; the systems in use cannot operate or withstand pressures greater that 500 psi. Further, the use of heat exchangers have been limited to coils placed into a bath of cryogen to allow for time consuming, inefficient passive subcooling of the cryogen in which activation of these devices circulate a cryogen (such as liquid nitrogen) to a probe to create a heat sink, thus resulting in tissue freezing.

There exists a need for improvements in cryotherapy, and medical devices or components associated with the treatment, to better circulate liquid cryogen to a cryoprobe, to provide for rapid delivery through small tubes, and to facilitate improved measures for treatment and cost. The system of the present invention will allow for the circulation (cooling, delivery, and return) of liquid cryogen to a cryoprobe for the freezing of targeted tissue. The invention will facilitate the eradication of tissue, decrease hospitalization time, limit postoperative morbidities, shorten return to daily functions and work, and further reduce the overall treatment cost. Desirably, these improvements to device design and application will also increase its utilization for the treatment of multiple disease states.

SUMMARY OF THE INVENTION

The following invention is a cryogenic medical device designed to deliver subcooled liquid cryogen to various configurations of cryoprobes for the treatment of damaged, diseased, cancerous or other unwanted tissues. The device is a closed or semi-closed system in which the liquid cryogen is contained in both the supply and return stages.

By converting liquid nitrogen to supercritical nitrogen (SCN) in a cylinder/cartridge cooled by atmospheric liquid nitrogen (−196° C.), the SCN can be subcooled and tuned to the liquid phase, attaining an excess temperature. When the SCN is injected into one or more flexible cryoprobes, the SCN flows with minimal friction to the tip of the probe. In the tip, SCN pressure drops due to an increased volume and outflow restriction, heat is absorbed (nucleate boiling) along the inner surface of the tip, micro bubbles of nitrogen gas condense back into a liquid, and the warmed SCN reverts to pressurized liquid nitrogen as it exits the return tube and resupplies the dewar containing atmospheric liquid nitrogen. This flow dynamic occurs within a few seconds, typically in the order of 1 to 10 seconds depending on the probe or attachment configuration, and is regulated by a high pressure solenoid valve. Further, once the instruments are in place, the cryosurgical procedure can be performed with freeze times in ranges of about 15 seconds to 5 minutes (or ranges thereof), a drastic improvement over current known methods. Upon emptying of the first cartridge subassembly, the process can be repeated with the second cartridge subassembly or any number of cartridges operated individually or in combination. Furthermore, embodiments of the present invention can be incorporated in any supercooling system or in delivering liquid cryogen to the desired instrument.

In one embodiment, the closed or semi-closed system has multiple pressurized cylinders filling and firing in sequence, and pressurized through a heating coil in one or more of the contained pressurized cylinders. The device is vented to the surrounding atmosphere through an adjustable pressure vent to prevent excess pressure buildup while in operation. The device comprises a number of parts including a vacuum insulated outer dewar, submersible cryogen pump, a series of self-pressurizing pulsatile delivery chambers, baffled linear heat exchanger, return chamber, and a series of valves to control the flow of the liquid cryogen. The outer dewar comprises a cryogenic apparatus having pressurizing pulsatile delivery chambers which drive liquid cryogen through the baffled linear heat exchanger. The linear heat exchanger comprises a tube-within-a-tube (i.e. chamber within a chamber configuration) whereby a vacuum is applied to the outer chamber to subcool an isolated reservoir of liquid cryogen. The inner chamber comprises a series of baffles and a central spiral to increase the flow path of the liquid cryogen while providing for increased contact-based surface area with the outer chamber to allow for more effective heat transfer and subcooling of the cryogen being delivered to the probe. Following circulation to the cryoprobe, cryogen (liquid and gas) is returned to the device into a return chamber which surrounds the supply chamber, thereby providing for a staged secondary subcooling chamber for the cryogen in the supply tube. The return chamber is open to the main dewar tank thereby allowing for exchange of liquid and gas between the supply and return chambers. Device operation is controlled and monitored by a series of pressure and vacuum valves designed to control the flow, cooling, and pressurization of the liquid cryogen. This control is achieved through various configurations of manual and computer controlled systems.

In one embodiment of the invention, a cryogenic catheter or probe designed to deliver cryogen (liquid or gas) for the treatment of damaged, diseased, cancerous or other unwanted tissues is disclosed. The product/device is a tube within a tube and comprises a number of parts including a supply and return tubes (i.e. internal tubes), outer sheath (i.e. external tube) sealed to the inner tubes at one or both ends with a gas filled lumen between the internal and external tubes. The lumen of the external tube is filled with a non-equilibrating saturated gas which solidifies upon cooling, thereby creating a vacuum along the length of the catheter to provide for insulation between the inner and outer tubes and preventing freezing along the length of the probe shaft. Further the outside surface of the internal tubes is modified to potentiate gas nucleation on the outer surface of the internal tubes upon cooling.

At the distal end or tip of the probe shaft, the internal tubes come into contact with the outer tube and create a defined region of ultra cold temperatures to cool and freeze the target tissue region. The catheter is designed to carry liquid cryogen under various pressures as well as liquid cryogens of varying temperatures. Delivery of cryogen to the catheter is provided by a cryogenic medical device console through the connection of the longitudinal body.

In one embodiment, a dual insulative barrier is capable of being formed. The device creates a temperature initiated transient vacuum insulation along the length of a catheter. The device further couples the temperature initiated vacuum with that of a surface modification along the inner tubes/lines to enhance nucleation and deposition of the saturated gas on the outer surface of the inner tubes to create an additional layer of insulation. The enhanced deposition or nucleation modification contributes by making the vacuum more effective. In addition, the saturated gas filled lumen of the outer tube at ambient temperature may be run at any given pressure. For exemplary purposes and not limitation, one embodiment maintains the pressure at atmospheric levels or may control the pressure to elevated or reduced levels.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion. Further, the below representations of a longitudinal body may not be drawn to scale where particular aspects extend the longitudinal body to lengths up to six feet and beyond (as dependent on the desired application).

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1:
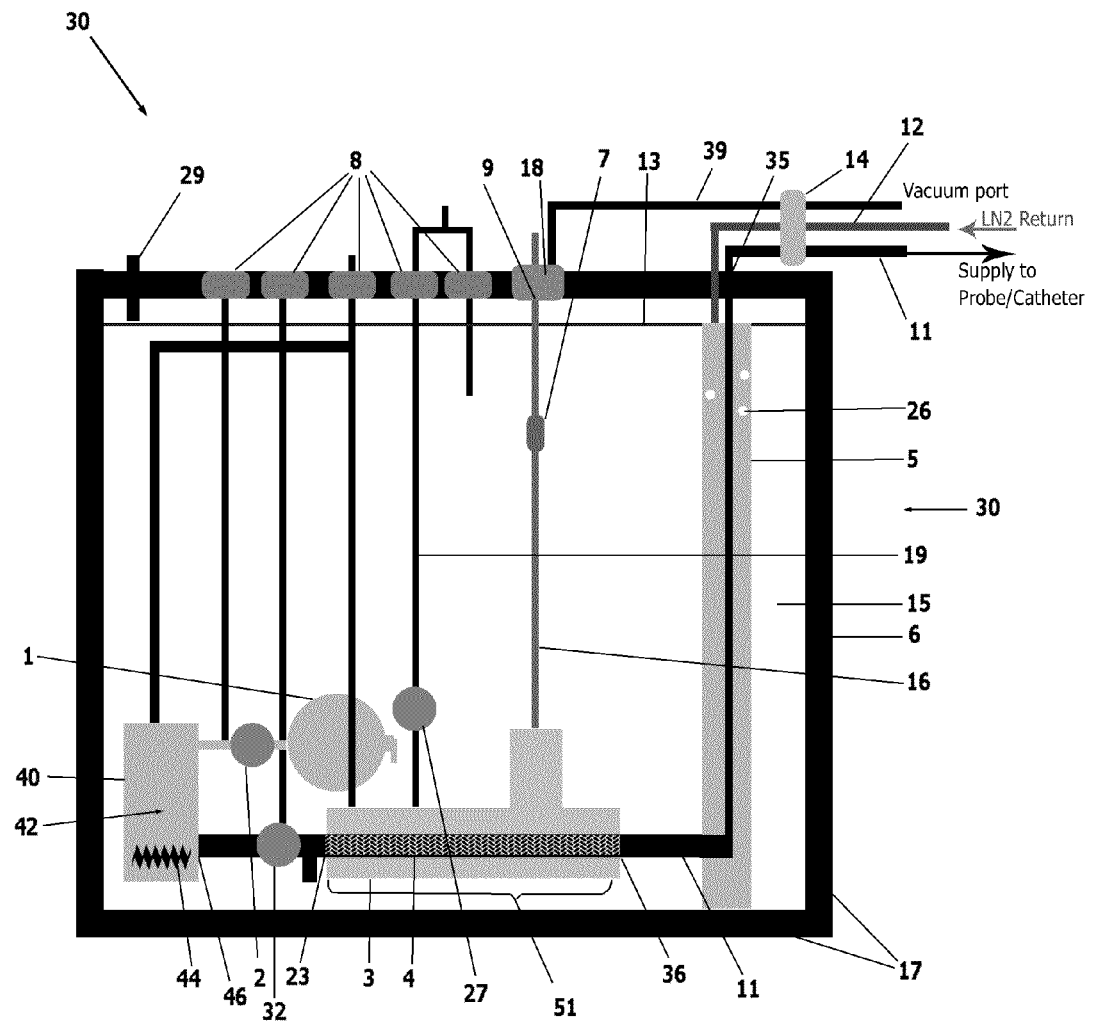
FIG. 1 is a side view of an illustrative embodiment of the device of the present invention.

An external view of a device and system in accordance with one embodiment of the present invention is shown in FIG. 1. The cryogenic system or device 30 has sidewalls 17 which form a container 6 that encloses an internal cavity, or lumen 15. In an embodiment of FIG. 1, the container 6 takes the form of a vacuum insulated dewar 6. The dewar 6 stores liquid cryogen and interconnects a supply line 11 and return line 12 to a probe or catheter (not shown) to form a closed system 30. The dewar 6 may be made of material such as stainless steel or any other material known for providing a vacuum insulated vessel. The dewar 6 is filled with liquid nitrogen or other liquefied gas (here, discussing as cryogen) to a maximum level 13. In one aspect, liquid nitrogen may be preferred. In another aspect, any fluidic cryogen may be utilized (e.g. argon, oxygen, helium, hydrogen).

Within the internal cavity 15 of the dewar 6 is a submersible pump 1 which delivers the liquid cryogen to a sealed pressurization apparatus 40. In one embodiment, a valve 2 controls the pressure fill into internal open chamber 42 of the pressurization apparatus 40. Once the cryogen enters the pressurization apparatus 40, an immersion heater 44 housed in the internal open chamber 42 heats the cryogen to create a desired pressure. The liquid nitrogen within the pressurized chamber starts at a temperature of about −196° C. When the heater is activated, it boils the nitrogen within the immediate area. Temperature within internal cavity 42 therefore stays within about −196° C. to −150° C., more typically in the range of about −196° C. to −160° C., or rather between about −170° C. to −160° C. Pressurized cryogen is then released through a valve 32 into the baffled linear heat exchanger 4. In one aspect, liquid nitrogen is converted to supercritical nitrogen (SCN) within the pressurization apparatus. The SCN is then directed to the heat exchanger for subcooling and tuned to the liquid phase to attain an excess temperature. Thereafter, the SCN can be injected into one or more flexible cryoprobes such that the SCN flows with minimal friction to the tip of the probe.

The baffled linear heat exchanger 4 in one embodiment is surrounded by a subcooling chamber 3 which subcools the pressurized cryogen for delivery to external cryoprobes. The subcooling chamber 3 in connection with the heat exchanger 4 at an entrance 23 and an exit opening 36 form an integral unit 51 for supplying subcooled liquid cryogen. From the heat exchanger 4, the subcooled cryogen passes into a supply line 11 and continues out through an exit port 35 and through a control valve 14 where various configurations of cryoprobes are attached. The subcooling chamber may attach a vent line to any of the vents 8, to a supply connecting line 19 controlled through a valve 27, or to a vacuum line 16 through a control valve 7 which is connected to a vacuum pump 18.

The cryogen is returned (as demonstrated by the arrows in FIG. 1) from the cryoprobe via a return tube 12 into a return chamber/cylinder 5 of the dewar 6. The return tube 12 connects into the return cylinder 5 which also surrounds the supply tube 11 that exits the heat exchanger 4. One or more exit ports 35 may be included in a side wall 17 of the dewar 6 or may be a separate unit 14 to incorporate various control valves.

In operation, the device 30 is filled through a supply port 29 and then sealed to form a closed system, thereby allowing for the supply, return, collection, and re-utilization of liquid cryogen during its utilization in the medical/surgical field. The entire system 30 may or may not be pressurized during operation. The system may also be vented to the surrounding environment to prevent excess pressure buildup during operation. In one aspect, the returning cryogen empties into the return cylinder or chamber 5. In another aspect, the returning cryogen may empty as bulk fluid into the internal lumen 15 within the dewar 6.

In one embodiment of the present invention, the linear heat exchanger 4 subcools the liquid cryogen prior to delivery to tissue. In the embodiment of FIG. 1, the linear heat exchanger 4 is an inner chamber 4 which passes through subcooling chamber 3 and is connected via the entrance 23 and exit opening 36. Liquid cryogen passing through the inner chamber 4 is reduced in temperature to a subcooling degree by the outer subcooling chamber 3. The chamber within a chamber configuration includes a subcooling vacuum chamber 3 filled with liquid cryogen upon which a vacuum 18 is drawn through valve-controlled port 9 to reduce the atmospheric pressure on the cryogen. The temperature of the cryogen within the subcooling chamber 3 can then be reduced even further. The subcooling chamber 3 also comprises valve controlled ports 8 external to the maximum liquid cryogen level for monitoring and electronically controlling temperatures, pressures, and flow rates of liquid cryogen passing through the subcooling unit. In one aspect, a vacuum 18 can be drawn on vacuum line 16 at a controlled internal valve 7 or external valve 9. In another aspect, valve controlled ports 8 may be accessible for delivery of liquid cryogen to the subcooling chamber 3 by way of a supply line 19 or as a vent 8 for any excessive gas coming from the subcooling chamber 3. As depicted in FIG. 1, the vacuum 18 also is attached to the cryoprobe(s) by way of vacuum line 39.

Figure 2:
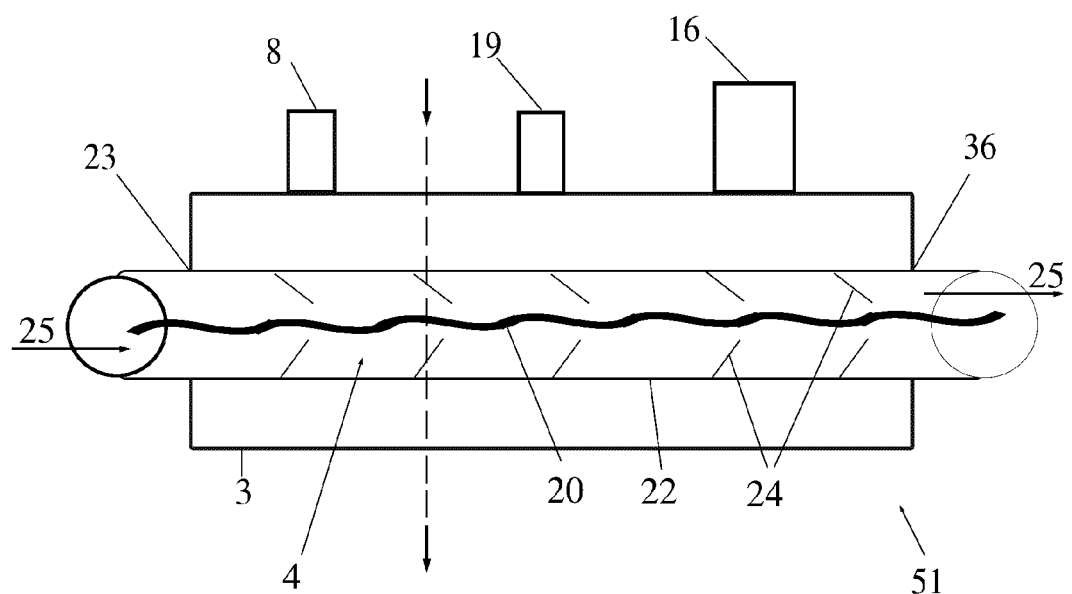
FIG. 2 is a side view of one embodiment of a heat exchanger of the present invention.
Figure 3:
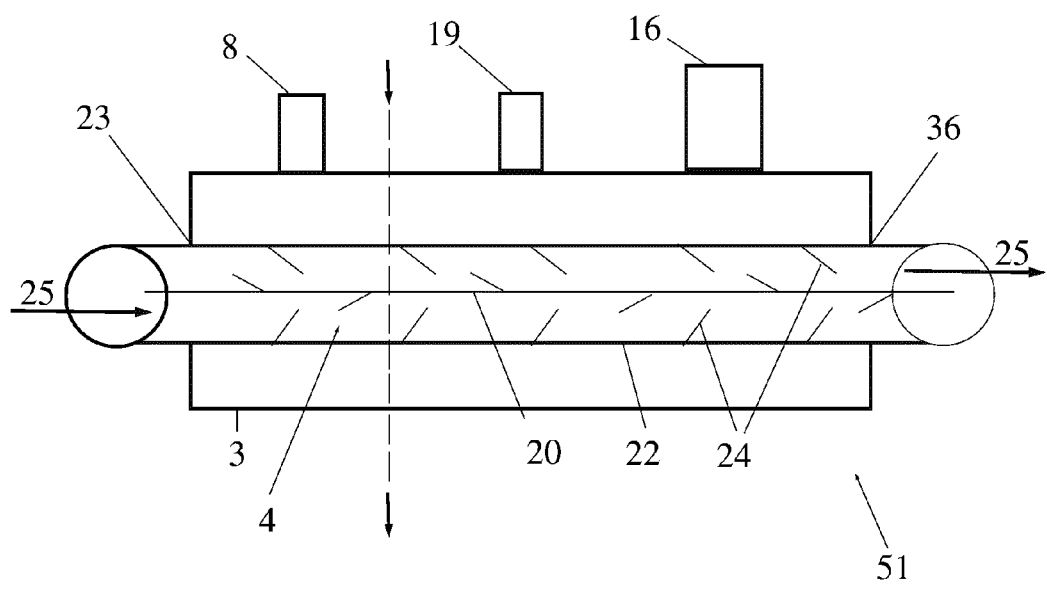
FIG. 3 illustrates a side view of one embodiment of a heat exchanger of the present invention.

Aspects of the linear heat exchanger 4 are illustrated in FIGS. 2 and 3. FIG. 2 and FIG. 3 illustrate side views of different aspects of a linear baffled heat exchanger 4 and subcooling unit 3 as an integral unit 51. An interior central component or spiral 20 within the interior lumen of the chamber 4 operates like a corkscrew to increase the flow path 25 of the liquid cryogen. An outer wall 22 of the inner chamber 4 also comprises baffles 24 which increase the surface area in the heat exchanger for quicker and reduced cooling of the liquid cryogen. As illustrated, a series of baffles 24 emanate into the flow path 25 (as illustrated by arrows) of the cryogen in the inner lumen, thereby increasing the surface area in the heat exchanger 4. The spiral component, however, may be any size and shape as to efficiently increase the flow of liquid cryogen. Planar structures, as described below, or any additional features included to increase surface area may be incorporated or substituted.

FIG. 3 illustrates another embodiment of a linear heat exchanger 4 such that the internal structure 20 has a planar configuration and also operates in a circular motion to increase the flow 25 of the liquid cryogen. An internal structure 20 assists in circulating the flow of liquid cryogen through the interior lumen of the chamber 4, possibly with an interconnected tubular unit that would allow radial movement of internal structure 20.

One embodiment of the medical device comprises a return chamber 5 which is illustrated as a return cylinder 5 in FIG. 1 such that the return chamber 5 surrounds the supply line 11 coming from the heat exchanger 4. The return chamber 5 and the surrounded supply line may then provide a secondary heat exchanger for the system/medical device 30. Cryogen return is vented into the return chamber 5. In one aspect, the return chamber 5 comprises a series of vent holes 26 near the top of the return chamber 5 to allow for the venting of gas and/or liquid overflow into the main dewar 6. Vent holes 26 allow for the reutilization of cryogen and thus extend the operation time for the medical device 30.

In another aspect, the return tube 12 is vented into the main dewar 6 either directly or by first passing through a linear heat exchanger (similar to the combination of heat exchanger 4 and subcooling chamber 3) to subcool the return cryogen prior to venting into the main dewar 6. Return of the cryogen to the main dewar 6 allows the cryogen to return through a heat exchanger such that the cryogen is reutilized and extends the operation time even longer.

In another embodiment, the medical device 30 may provide a system which is controlled through a series of computer controlled valves including any heaters, sensors, motors, or gauges. The sensors control and monitor pressure, temperature, and fluid level in the dewar, and can measure any metric as may be desired. In one aspect, the sensors monitor pressure levels within defined safety ranges. In another aspect, the sensors may control the pressurization of one or more components internal to the dewar. Any of the valves 2, 7, 8, 9, 27 or 32 including exit portal valve 14, may be automated to enable a controlled and consistent operation of the cryogenic system (e.g. computer controlled operation through the electronically controlled valves).

Figure 4:
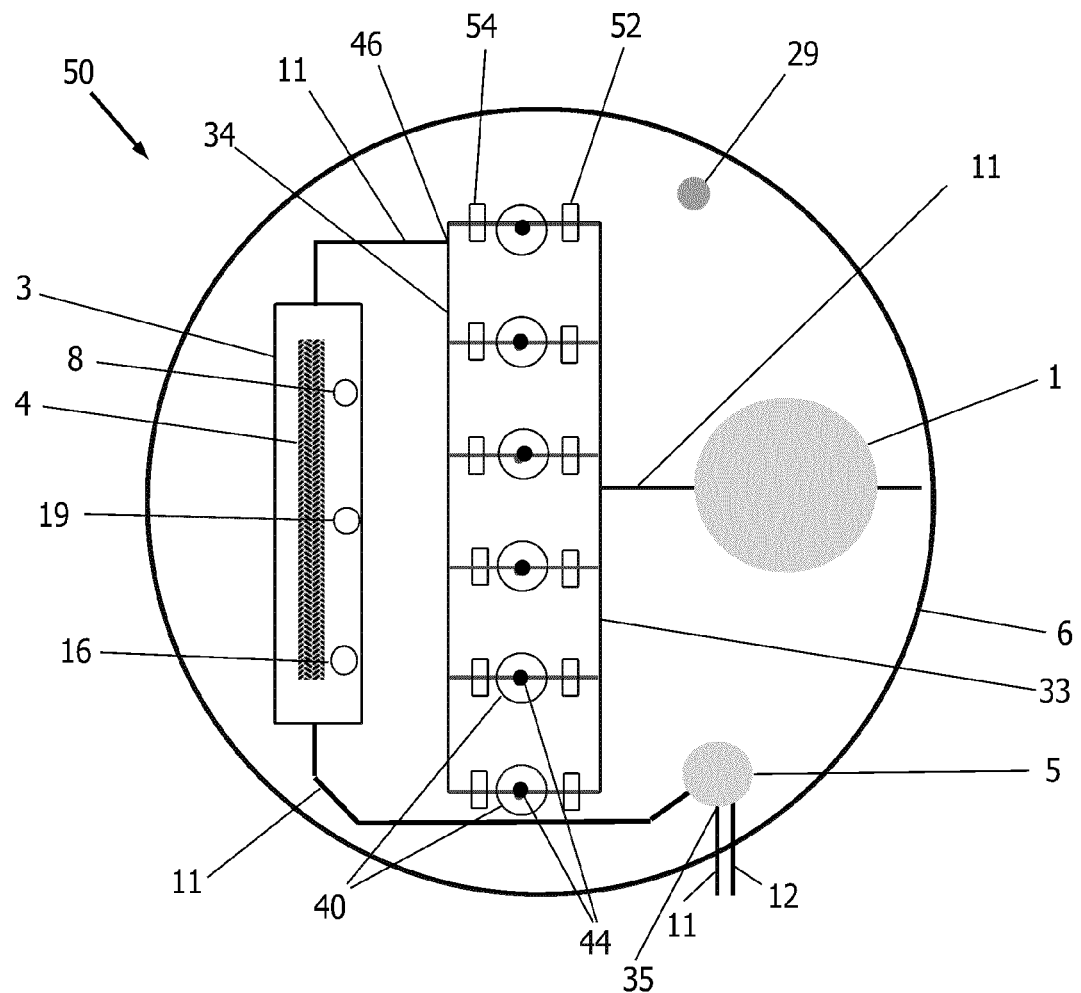
FIG. 4 is a top view of one embodiment of a device of the invention.

An embodiment of a system 50 is shown in FIG. 4. As illustrated in a top view of the system 50, a series of six pulsatile pressurization chambers 40 are sealed chambers/cylinders 40 within dewar 6 of the closed system 50. From the pump, liquid cryogen in pumped to the pulsatile pressurization chambers 40 which then delivers liquid cryogen in a continuous series of bursts to the heat exchanger 4. The baffled linear heat exchanger 4 provides an enhanced subcooling of the pressurized liquid cryogen while also incorporating an integral subcooling unit 3. The chambers 40, each comprising an individual immersion heater 44, can then sequentially deliver liquid cryogen at consistent rates, or as specifically determined rates, to the heat exchanger 4.

From the heat exchanger, the subcooled cryogen passes into a supply line 11 and continues out through an exit port 35 where a control valve 14 is positioned and various configurations of cryoprobes are attached. The cryogen is returned (as demonstrated by the arrows in FIG. 4) via a return tube 12 from the cryoprobe to the dewar 6 into a return cylinder 5. The return tube 12 connects into the return cylinder which surrounds the supply tube 11 that exits the heat exchanger 4. The entire system 50 may or may not be pressurized during operation. The device is also vented through vent ports 8 to the surrounding environment to prevent excess pressure buildup during operation.

During the operation of the system 50, as illustrated in the embodiment of FIG. 4, a cryogenic system 50 has been filled and detached from its cryogenic fill tank. In one embodiment, the system 50 is a separate mobile unit protected and contained entirely within an enclosed console for easy access and mobility. Once the system has been sealed, the cryogenic supply can be maintained for several procedures. The reutilization of the liquid cryogen provides a time savings and cost-efficient model for cryotherapeutic and cryosurgical procedures. The system 50 can be further utilized for any process requiring rapid cooling.

As depicted, the system 50 comprises a submersible liquid nitrogen pump 1 connected to a supply line 11 which directs the liquid nitrogen into a supply manifold 33. The supply manifold 33 routes the liquid nitrogen into at least one pulsatile pressurization chamber 40 where the liquid cryogen is heated. The pressurized liquid cryogen, here, liquid nitrogen, then starts filling the next pressurization cylinder/chamber 40 in the series such that when one chamber 40 is filling, another can be simultaneously pressurized and prepared for use. This permits a wave of activity through the cylinders so that it can cycle through each step of system operation. As the pressurized cryogen is delivered to the heat exchanger 4, and passes the subcooled pressurized cryogen out through the supply line 11 through the exit port 35 and into the attached cryoprobes, another pressurization chamber is filled and pressurized. The simultaneous use and pressurization of the liquid cryogen provides for the sequential delivery of liquid cryogen in a continuous series of pulsations to a cryogenic instrument or probe.

In one embodiment, liquid nitrogen is used; however, any cryogenic fluid may be utilized, including nitrogen, argon, helium, hydrogen, and other such desired fluids. Each pressurization apparatus 40 comprises a pressure valve controlled inlet 52, valve controlled outlet 54, and vent ports as may be desired, as well as an immersion heater 44. In one aspect, the filling of the pressurization apparati 40 is controlled through a series of pressure valves 52 on the supply manifold 33. Liquid cryogen is heated within each pressurized apparatus. Pressurized liquid cryogen is then released through the control valve 54 to an outlet port/opening 46 of an outlet manifold 34 to the supply line 11, and delivered to a baffled linear heat exchanger 4. In the illustrated embodiment, a subcooling unit 3 surrounds the heat exchanger 4 for more rapid cooling.

In one embodiment, the cryogenic device 50 comprises six pressurized apparati 40 linked together. Other embodiments, however, may comprise any number of pressurized apparati 40 individually or linked together in combination. The apparati can then be controlled individually or in sequence to deliver pressurized liquid cryogen to the heat exchanger 4. In another aspect, one or more pressurization apparati 40 may be arranged to supply one or more cryoprobes. Further, the series of pressurized apparati 40 may be interconnected with another series of apparati 40.

In the embodiment of FIG. 4, six pulsatile pressurization chambers 40 are housed within a support network of a console. In one example, three of the cylinders within one-half of the dewar simultaneously fill while three cylinders within the other half of the dewar deliver cryogen out through the outlet manifold. (Any number of cylinders, however, may be operated individually or in desirable combinations.) Liquid cryogen is heated in the sealed pressurization chambers 40. Pressure is increased to a specified level in the sealed pressurization chambers 40, and then the pressurized cryogen is controllably released into a heat exchanger 4 to subcool the cryogen. In one aspect, a subcooling vacuum chamber 3 surrounds the heat exchanger 4, facilitating the delivery of subcooled cryogen to an attached cryoprobe (also referred to as probe or catheter). As the pressurized cryogen is utilized, a sensor within the heat exchanger monitors the temperature and pressure of the subcooled cryogen passing into supply line 11 as it continues out through an exit port 35 where various configurations of cryoprobes are attached.

Although the system may fill or discharge each cylinder 40 individually, any simultaneous fill or discharge, or rate of fill or discharge, may be incorporated into the system. The closed system keeps a constant supply of liquid nitrogen available for delivery to the cryoprobe and provides a more immediate and rapid rate of cooling for cryotherapeutic procedures. It is therefore possible to close the supply port 29 where supply tanks fill the dewar (See FIG. 1 and FIG. 4) and move the system to any locale or setting. Furthermore, as depicted in FIG. 1, the supply valve 2 may be closed and the release valve 14 opened to create a flow of liquid cryogen to the cryoprobe. Various arrangements of valves and sensors may therefore provide for similar flow.

In one embodiment, the pressurized chambers 40 are filled and the dewar sealed. A single drive pump 1 perpetuates directional flow of the cryogen into the pressurization chambers. In one embodiment, all chambers can be filled through various configurations of single direction pumping. In another embodiment, a reversible pump and fill method allows one pressurized chamber 40 to fill and then the pump 1 flips or reverses functionality to fill another pressurized chamber. This process can be repeated to fill any number of chambers.

In one embodiment, pressurized chambers 40 are enclosed completely within the dewar 6. However, any arrangement of the pressurized cylinders is possible so long as the closed system provides for the pulsatile delivery of cryogen to the cryoprobe. As such, any single or multiple configurations of cryoprobes or catheters may be used. Such instruments may also include cryoguns or cryodevices for rapid cryo-delivery processes or cryotherapies.

Figure 5:
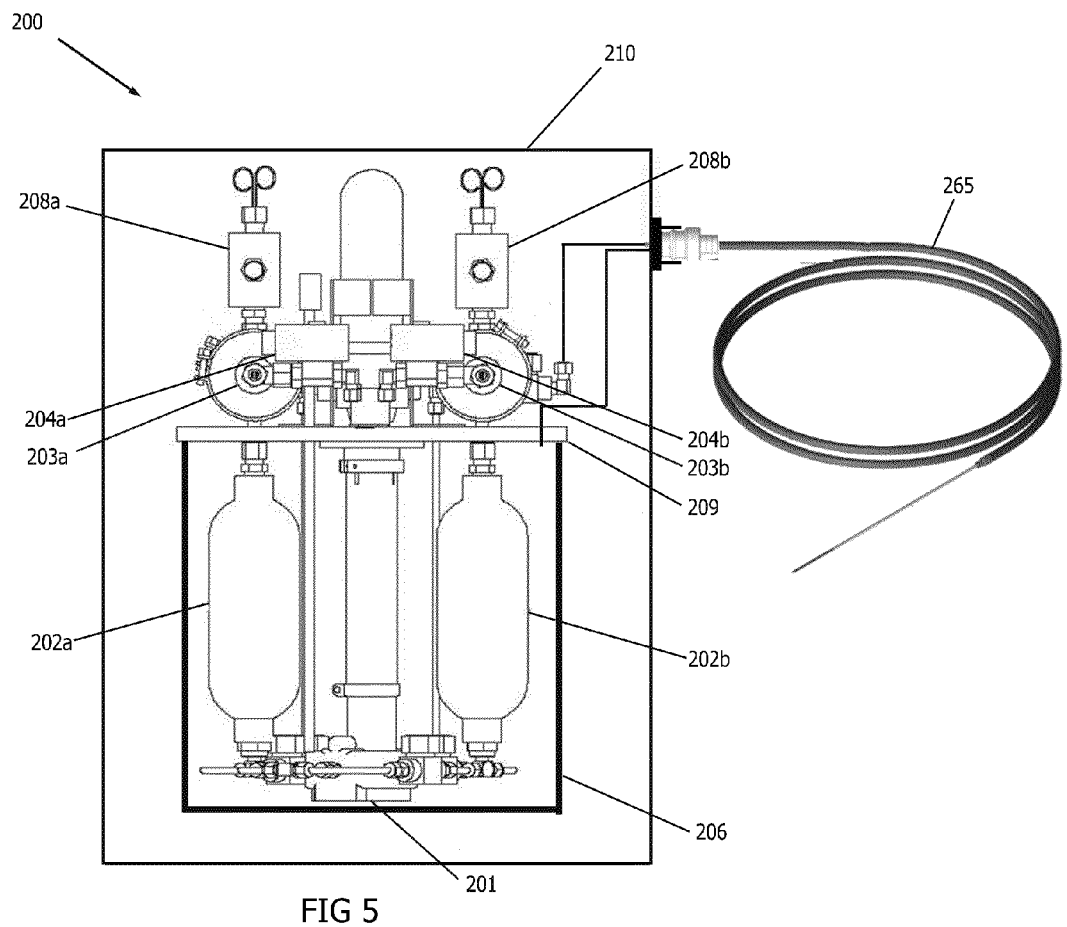
FIG. 5 is a depiction of a front view of the system.

As illustrated in FIG. 5, a cryogenic system 200 (also known as cryoengine 200) has a two cylinder configuration, the system of which is divided into two subassemblies: (I) those components above the cover 209 and (II) those components below the cover. All of the components below the cover are contained in a liquid nitrogen dewar 206 and immersed in liquid nitrogen at atmospheric pressure (BP=−196° C.) during operation. The machinery and components of the operational system are housed in a console 210 to which the cryocatheters/cryoprobes 265 are attached to form the complete system 200. To understand the operational features of the cryoengine and method of production and transport of supercritical nitrogen (SCN), a brief description of cryogen flow follows.

Upon filling the dewar 206 with liquid nitrogen from an external source, an immersible liquid cryogen pump 201 is activated to fill each cryogen supply cylinder 202*a* & 202*b*, or cartridge, sequentially. Initially, one cartridge 202*a* is filled along with its linked cryogen pressurization cartridge 203*a*. Cryogenic solenoid valves 204 (a and b) provide venting of the gas within the cartridge assembly to support filling. Manifolds 208 (typically metal, stainless steel or aluminum) provide access points into the cartridges/cylinders 202, 203. The manifolds comprise components such as a heater, thermocouple, and the vent lines that pass through to the cylinders 202, 203. Upon completion of the filling process, the cryogen pressurization cartridge 203*a* is heated to generate a pressure of about 1000 psi (68 bar). Liquid nitrogen becomes critical at about 493 psi (34 bar) (BP=−147° C.). Pressurization beyond the critical point results in the formation of SCN, a dense fluid without surface tension and capable of frictionless flow, and with properties that may be tuned to either a gas or liquid.

By converting liquid nitrogen to SCN in a cartridge cooled by atmospheric liquid nitrogen (−196° C.), the SCN is subcooled and tuned to the liquid phase, attaining an excess temperature (i.e. the ability to absorb heat without boiling) of approximately 50° C. When the SCN is injected into the flexible cryoprobe, the SCN flows with minimal friction to the tip of the probe (boiling chamber). In the tip, SCN pressure drops due to an increased volume and outflow restriction, heat is absorbed (nucleate boiling) along the inner surface of the TIP, micro bubbles of nitrogen gas condense back into a liquid, and the warmed SCN reverts to pressurized liquid nitrogen as it exits the return tube and resupplies the dewar containing atmospheric liquid nitrogen. This flow dynamic occurs within a few seconds and is regulated by a high pressure solenoid valve 204. Upon emptying of the first cartridge subassembly (202a & 203a), the process is repeated with the second cartridge subassembly (202b & 203b).

As demonstrated by FIG. 5, the limitations of liquid nitrogen have been overcome by developing a novel device to convert atmospheric liquid nitrogen to supercritical nitrogen. Where liquid nitrogen was previously delivered through large tubes and did not provide for rapid delivery, the current system herein described allows for rapid delivery of liquid cryogens through very small tubing of the cryo-instrument 265. The SCN can be injected or drawn through two plus meters of hypodermic tubing without boiling, thereby resulting in near instantaneous ice formation at the tip to target site specific ablation of tissue as well as the creation of transmural lesions without the formation of a thrombus or aneurysm. Supercritical nitrogen is a dense fluid with properties of both gas and liquid that can be tuned toward one phase or the other. In the liquid phase, SCN lacks surface tension and transports without friction. The above-described technology generates SCN in a pressurized cartridge immersed in atmospheric liquid nitrogen. This cryoengine, which operates as a cryogen generator, produces SCN in the liquid phase with a boiling point of about −149° C. which is subcooled by the surrounding atmospheric liquid nitrogen to about −196° C. When the SCN is expelled from the device to the probe tip, the SCN passes instantly through the system without the phase transition to a gas due to both the frictionless flow and the subcooling which compensates for parasitic heat gain along the path. As such, the embodiment of FIG. 5 may be utilized in any supercooling system or in directing flow of liquid cryogen through to a cryo-instrument. The supercritical point will be determined by the chemistry of the specified liquid or gas used. Therefore, the system can be adjusted to accommodate for differences in chemistry. A catheter/probe assembly 265 is connected to the cryoengine of FIG. 5.

Figure 6:
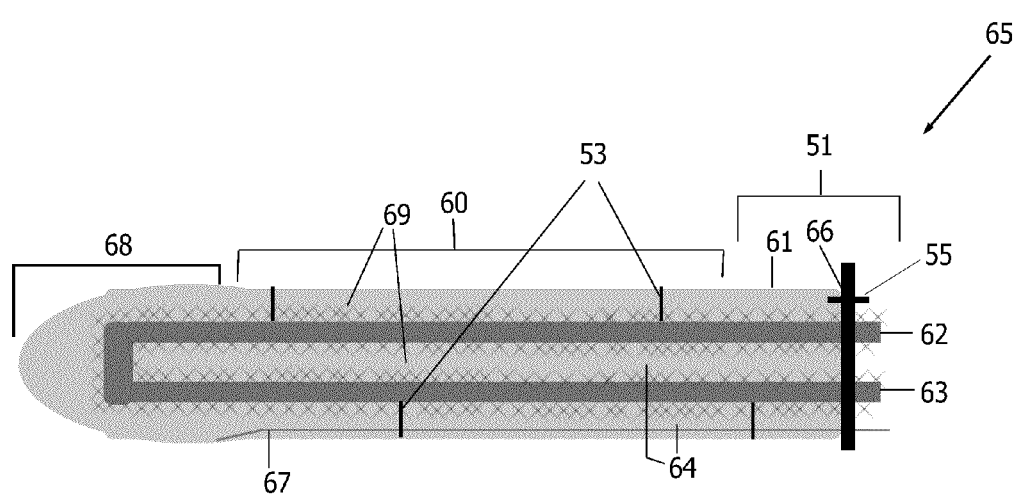
FIG. 6 is a side view of an illustrative embodiment of the device of the disclosed invention when the lumen is filled with particles in gaseous state.
Figure 7:
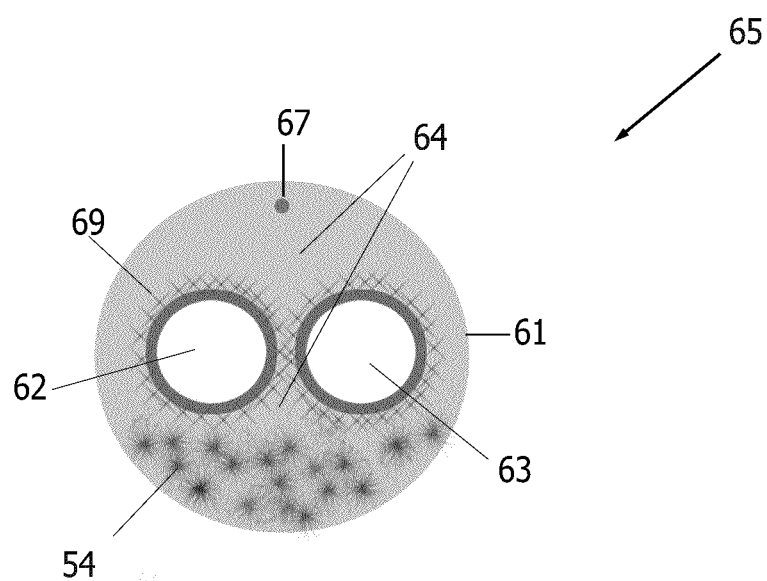
FIG. 7 is a cross-sectional view of the illustrative embodiment in FIG. 6.

An external view of a device 65 in accordance with one embodiment of the present invention is shown in FIG. 6 and FIG. 7. The device 65 of an embodiment takes the form of a catheter having a tube within a tube configuration, and forming the longitudinal body 65. The longitudinal body 65 comprises internal tubes, including a supply line 62 and a return line 63, contained within an outer insulation tube 61 and continuously running through the length of the tubular shaft 60 of the longitudinal body 65. The outer insulation tube 61, or outer catheter sheath 61, defines the size, shape, and dimensions of the longitudinal body 65 which conforms to dimensions that are capable of housing the internal lines 62, 63. The tubular shaft therefore extends from a proximal end 51 of the longitudinal body 65 to a distal end or tip 68. The outer catheter sheath 61 provides a unitary support structure for the flow of cryogen to and from the distal end of the catheter tip 68; desirably, the distal end is where a freezing event is initiated. The cryogen utilized in one embodiment may be liquid nitrogen. In another embodiment, supercritical nitrogen is utilized. Any desired liquid cryogen may be utilized, however, and the system adjusted to accommodate for different chemistries and phases of matter.

The inner supply line 62 and return line 63 are maintained in the center of the outer sheath 61 by open configuration insulative spacers 53 placed throughout the catheter 65. The open configuration allows for a catheter lumen 64 to be filled with gas. The outer catheter sheath 61 is sealed to the connector 66 to create the gaseous lumen 64. The tip 68, in combination with the inner supply line 62 and the return line 63 come into contact with the outer sheath 61 at the distal end to develop a freezing region.

In addition, in one embodiment, the shaft 60 of the catheter 65 is flexible, as facilitated by a deflection wire 67 that runs along the shaft 60, the shaft of which is insulated by a temperature induced vacuum. The deflection wire 67 is a control line that runs down the shaft 60 to the tip of the catheter 65 to allow the catheter tip 68 to be moved on an angle, in a finger-like motion to steer and direct the catheter/probe 65 to the target tissue. In one embodiment, the deflection wire 67 guides the device 65 and monitors environmental measures of temperature, pressure, and/or physiological conditions. The guide 67 may integrate individual components and sensors such as an optical imaging component in connection with the guide or any number of thermocouples, pressure transducers, electrocardiogram monitors, or other electrophysiological sensors, alone or in combination.

Another embodiment of the present invention may use insulative foam (e.g. styrofoam, plastics, rubberized materials or other such insulative compositions) to separate the outer shaft 60 from the internal lines 62, 63 (i.e. inner supply line 62 and return line 63). Various aspects of the invention, however, accommodate a catheter tip 68 as designed to be steerable and deflectable to allow for guided targeting to the desired tissue site. In one aspect, spacers or insulative foam may be utilized to prevent internal supply and return lines from contacting the outer sheath. In another aspect, any freeze zone can be produced as designated by the configurations of catheter tips 68. (See FIGS. 10-13).

In the process of utilizing the catheter 65 of the present invention, a condensation based vacuum insulation is temperature dependent and located in the catheter 65. Upon the outer surfaces 69 of the walls of the supply line 62 and return line 63, a process of physically marking or chemically etching the surfaces 69 enhances nucleation and physical vaporization deposition of saturated gas. For exemplary purposes only and not limitation, the surface may be roughened, sprayed with any number of powder-like substances like silica, metallic particles and/or a carbon coating. The lumen 64 within the outer sheath 61 is filled with select vapors, or non-equilibrated phase change gas 64. In this embodiment, for example, butane is utilized which remains in a gaseous state at about room temperature, between about 0° C. to about 37° C. (See FIGS. 6, 7), but solidifies into crystalline deposits 52 upon chilling to below about 0° C., and simultaneously deposits a film of crystals in a controlled deposition process upon the designated surfaces 69 (See FIGS. 8, 9). It should be noted, however, that the temperature variations are dependent upon the type of vapors utilized, chemical characteristics and variations of vapor combinations. Therefore, temperatures of varying gases may be selectively controlled so as to create the same or similar effect of spontaneous nucleation and simultaneous deposition upon reaching a freezing temperature.

In addition, one embodiment may interconnect a vacuum line of a cryosystem console with the catheter or probe 65 through a vacuum port 55 of the connector 66 as illustrated in FIGS. 6 and 7. In one aspect, the vacuum is formed upon sealing the lumen at the connector and mechanically drawing a vacuum through vacuum port 55. In another aspect, the vacuum port may connect via its own vacuum system or in combination with the vacuum pump of the cryosystem. Thus, a dual insulative barrier can be created in the present invention by either a mechanically drawn vacuum or a spontaneously induced vacuum [via temperature inducement] (the vacuum itself creating the insulation for the internal tubes) in combination with a nucleation enhanced surface modification to enhance deposition of gas crystals onto the designated outer surfaces of the internal tubes. Desirably, the outer walls of the internal tubes are physically or chemically etched at designated sites along the tubular shaft. A region within the distal end or tip 8 can then be configured specifically designated freeze zones.

Figure 8:
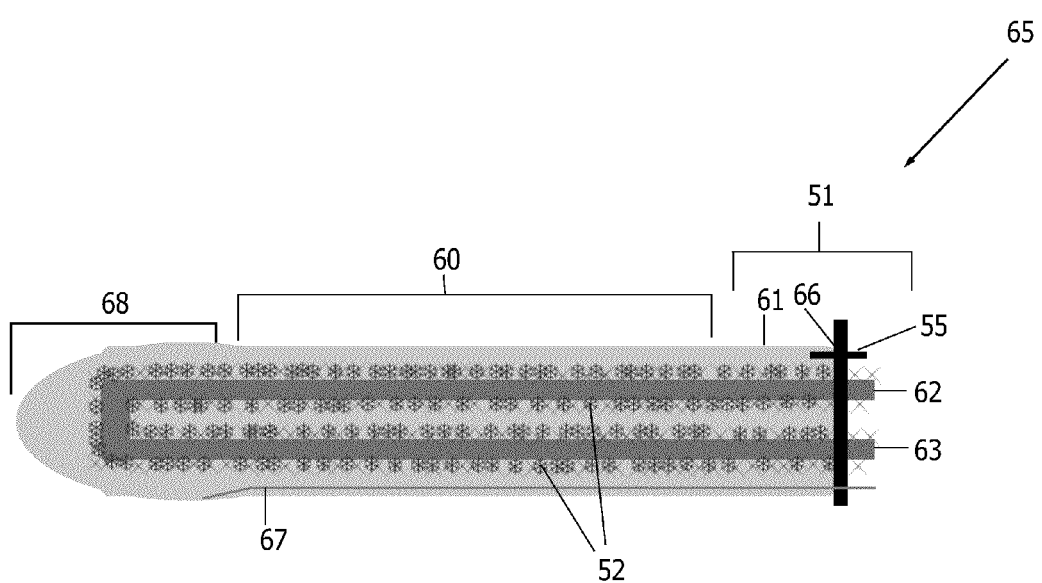
FIG. 8 is a side view of an illustrative embodiment of the device of the disclosed invention as temperatures are reduced to a freezing point of the particular gas selected.
Figure 9:
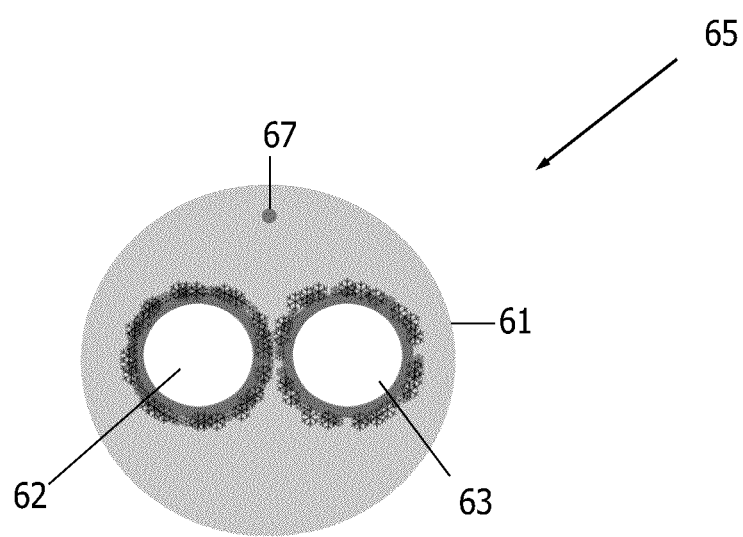
FIG. 9 is a cross-sectional view of the illustrative embodiment in FIG. 8.
Figure 10:
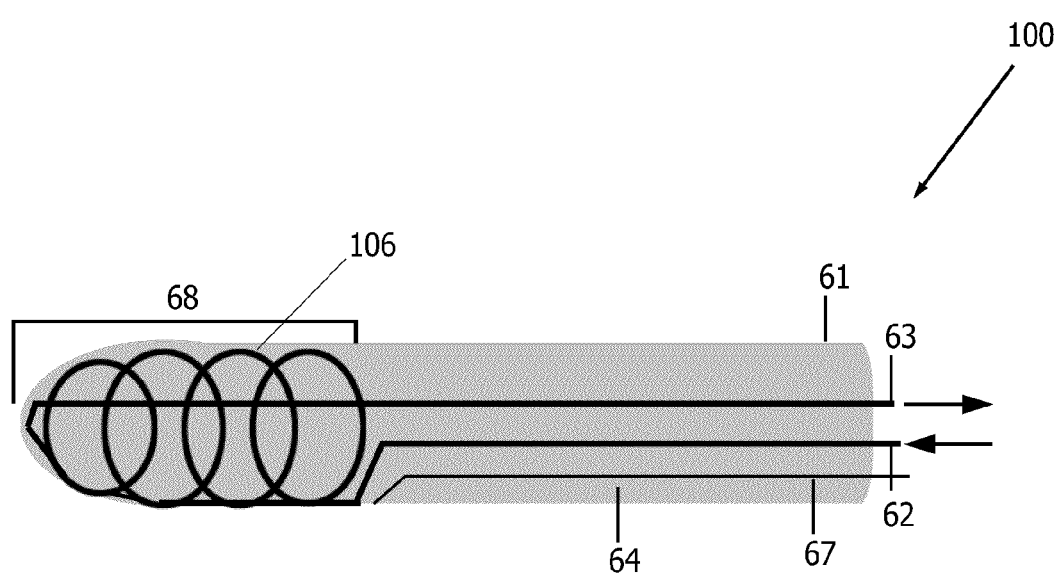
FIGS. 10-13 are side views of various embodiments of a device of the invention.

In the described embodiments, nucleation/ sublimation in combination with a deposition process forms solid crystals along the supply line 62 and return line 63 outer walls, and spontaneously results in an evacuated space within the lumen 64. The evacuated space acts as an insulative barrier between the outer catheter sheath and the frost encased inner lines 62, 63. Film wise deposition along a length of the surfaces 69 of the supply line 62 and return line 63 results in crystalline film deposits of low thermal conductivity. The deposition may coat a portion of the outer surfaces or the entire outer surfaces of the inner lines to run the entire length of the internal tubes. (Note: The 'x' marks in FIGS. 6, 7 demonstrate the nucleation enriched supply and return tubular surfaces 69, the tubular surfaces of which are modified by processes described herein. The non-solidified gas crystals 54, non-equilibrating phase change gas particles 54, are illustrated in FIG. 7. Nucleated or solidified particles, as designated by "*" are depicted in FIGS. 8, 9 upon the modifications "x" (etching) on the surfaces 69. The nucleated particles 52 (marked as "*") are formed when the gas reaches a freezing temperature. In one aspect, any pressure may be utilized. For exemplary purposes and not limitation, pressure in the device may be maintained or controllably elevated or reduced. For instance, gas may be maintained at atmospheric or high pressure to support the retention of the vapor state at room temperature.

Other aspects of embodiments of the present invention include gas as either a pure component or as a mixture of various components. Such gaseous compositions, for exemplary purposes only and not limitation, may comprise butane, carbon dioxide, iodine, camphor, and/or nitrous oxide.

In another embodiment, an enhanced nucleation surface 69 on inner tube/line 62, 63 surfaces may result where a process includes treating the walls of the inner lines 62, 63 to match nucleating efficiency with the chemical characteristics of the gas to be deposited (e.g. marking the surfaces with impurities, utilizing silica, or other powderized material, chemically coating or etching) and thereby create a similar effect.

Embodiments of the present invention manipulate the structural configurations of the tips 68, as illustrated in FIGS. 10-13. In one or more embodiments depicted, the freeze zone is created where the internal components 62/63 contact the outer sheath 61 at a distal end 68. One such embodiment of a distal end 100 in FIG. 10 includes a closed loop coiled supply tube 106 in contact with the outer sheath 61 to affect a cold sink. The supply line 62 and return line 63 convene at the freezing zone of the tip in the formation of a coil 106.

Figure 11:
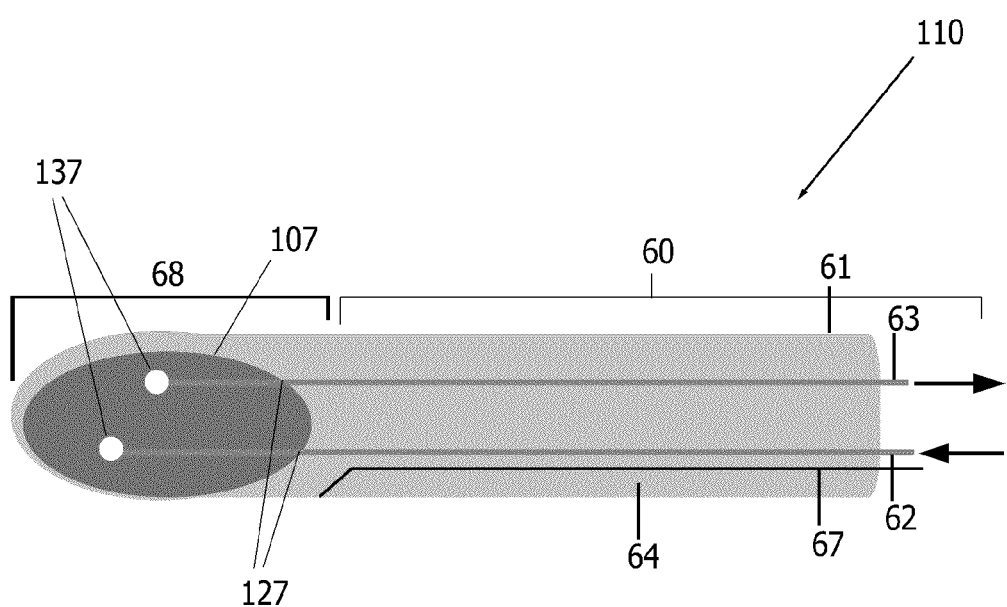

In another embodiment of a distal end 110, as shown in FIG. 11, a metallic balloon tip 107 is illustrated in which cryogen is circulated in the tip and then returned. The supply line 62 extends to a distance into the tip 68 beyond the extension of return line 63 such that cryogen pumped into the balloon-like tip 107 circulates within the sealed confines of the inflated region when the catheter is engaged for the procedure. The supply line 62, however, can extend any length or distance into the tip. The balloon-like tip may be composed of any flexible or rigid material including metallic, plastic, or ceramic compositions. Similarly, the balloon-like structure within the sheath may cause the outer sheath 61 to inflate and deflate for cryogenic procedures. For example, and not limitation, cryogenic procedures performed within a vessel may advantageously make use of an inflatable cryogenic element 107 at the distal end of the probe so that the outer sheath expands as the internal inflatable cryogenic element expands.

Also depicted in FIG. 11, the inflatable tip 107 is a sealed within the distal portion 68 in connection with both an individual supply line 62 and an individual return line 63. The embodiment of the distal end 110 is included in the length of the longitudinal tube and has a distal tip 68 which serves as the freezing region in connection with the tubular shaft 60 (only a portion of which is illustrated here in FIG. 11) (i.e. In the embodiment shown in FIG. 14, a distal end 128 can be replaced with distal end 110.) A sealed interface 127 ensures that the inflatable area can expand and contract in correspondence with the fill and removal of the cryogenic medium. The cryogenic medium in one embodiment in liquid nitrogen. Any cryogen may be utilized, however, to accommodate the demands of the system and treatment measures. Further, the inflatable structure, here, a metallic balloon tip, is designed and configured with materials that conform to the use of liquid nitrogen. Without considering the type of cryogen utilized, the inflatable tip may rupture or create undesired effects. For exemplary purposes, and not limitation, the tip of the present embodiment is designed to meet the needs of a system and device utilizing liquid nitrogen.

Another aspect of the probe/system in FIG. 11 is that the sealed interface 127 may be a wall or connection component (not illustrated) which seals the freezing region 68 of the tip away from the tubular shaft 60 in a blunt-tip probe. The sealed interface allows a supply line 62 and a return line 63 to access the freezing tip, the open ends 137 of which allow cryogen to be dispersed within the sealed zone 68. In FIG. 11, the sealed zone is the balloon tip, but any size or shape of sealed zone may be utilized in different aspects of the present invention to create similar results. It should be noted that the open-ended supply line in one embodiment extends further into the sealed zone toward the distal end and beyond the open end of the return line. Any length of supply line or return line, however, may be utilized; the lengths may be designed having equal lengths or different lengths, as desired.

Figure 12:
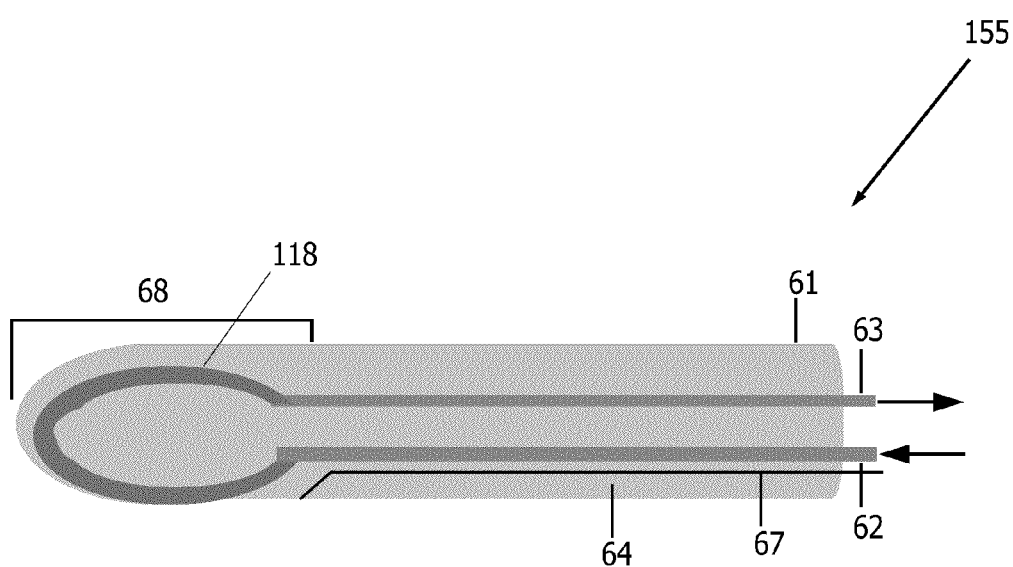

FIG. 12 is another embodiment of the probe tip/distal end 155 which illustrates a closed loop tip 118. The closed loop tip integrally connects both supply line 62 and return line 63 to form a unitary structure for delivery and return of liquid cryogen to the distal end in the freezing region of the probe.

Figure 13:
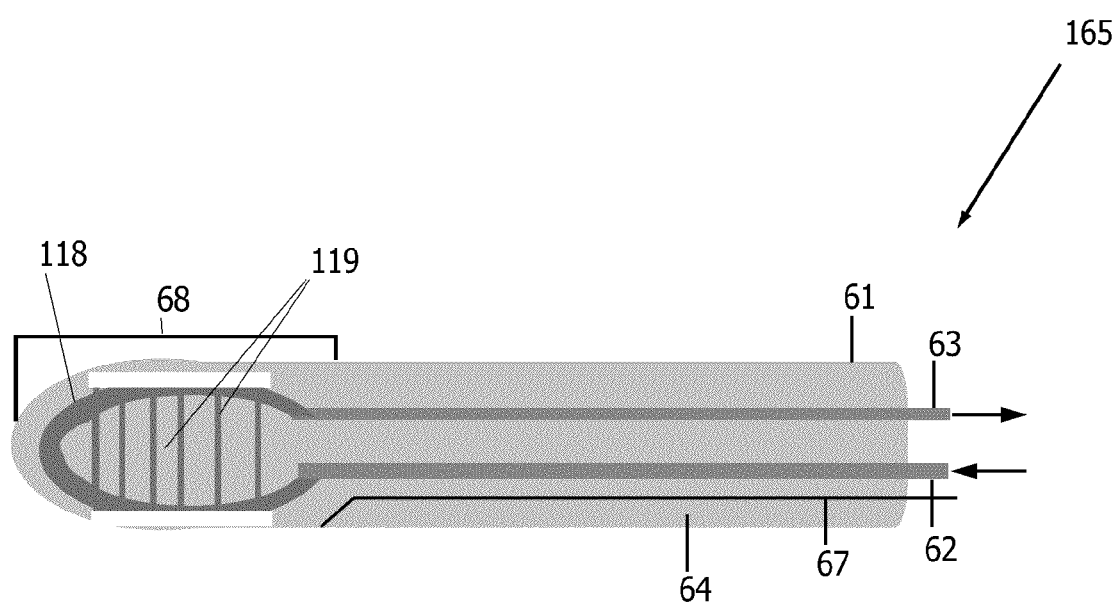

FIG. 13 illustrates a cryoprobe 165 as a closed loop tip with a finned heat exchanger 119 within the freezing zone or tip 68. The heat exchanger provides for a more efficient heat extraction from the tissue, thereby providing faster cryotreatment and greater injury/freezing to the tissue site. The heat exchanger is also utilized to cool the cryogen prior to return to the console, resulting in increased cryogen recovery. Other variations in tip design may be any size and dimension or take the size or shape of known catheters or probes 65 in the field.

For exemplary purposes and not limitation, in cancer therapeutics, cryoprobes are utilized to ablate the target tissue. In cardiac applications, catheters or surgical probes are utilized in the cryoablation procedure. Further configurations of the cryoprobe as described infra may also accommodate other structural variations.

Figure 14:
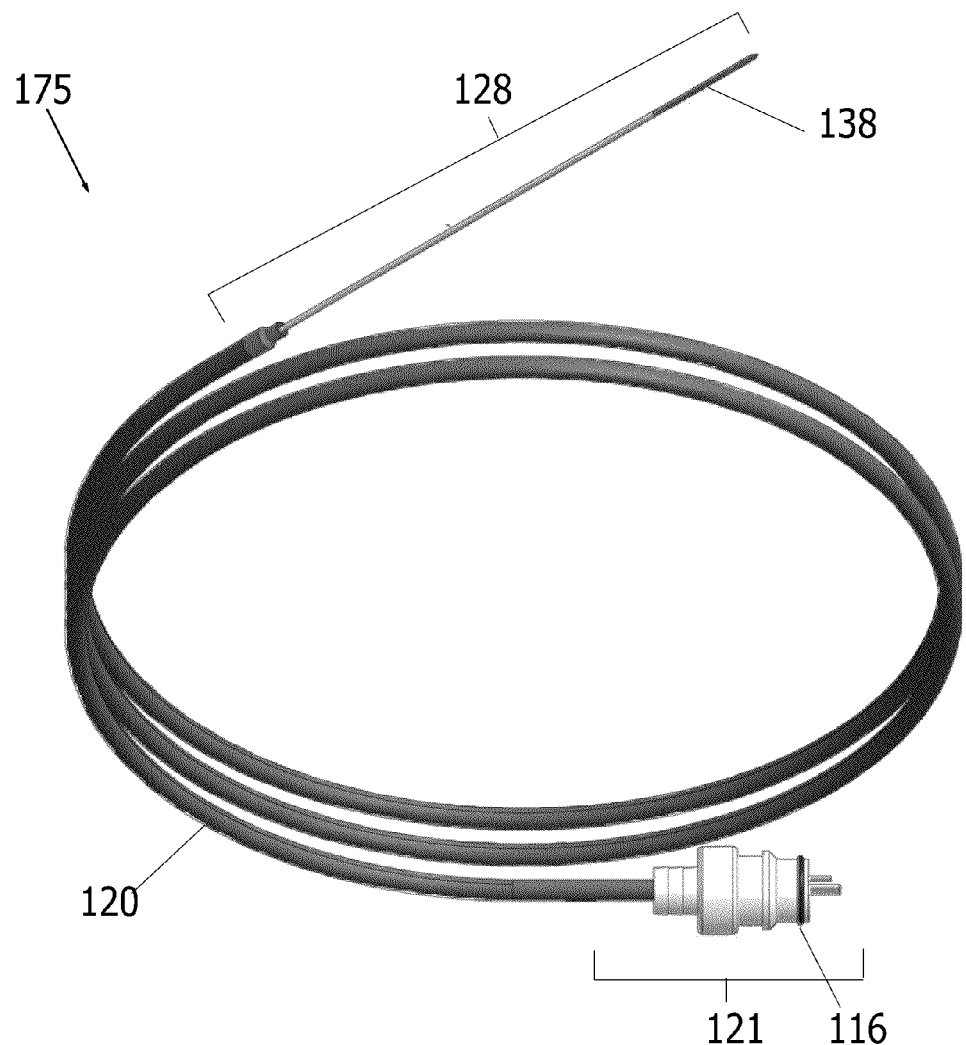
FIG. 14 is an illustrative embodiment of a product of the present invention.

As demonstrated in FIG. 14, the product for performing cryotherapeutic procedures is illustrated as an elongated body 175, about six feet in length. A connector 116 at a proximal end 121 allows the cryoprobe to be connected with a cryogenic delivery system 200 (see FIG. 5). The freezing region, or tip 138 is position within the distal end 128 with a flexible tubular shaft 120 positioned between the ends. (Some of the various embodiments of distal end 128 have been depicted in FIGS. 10-13, embodiments of distal ends 100, 110, 155, 165 which can serve as replacements for the distal end 128 within the elongated product 175. The support structure 175 comprises an outer sheath (as illustrated in FIGS. 6 and 7) which has at least one internal tube configured inside the sheath to deliver and return liquid cryogen to and from the freezing region/zone at the target tissue site. When in use and hooked to a cryogenic delivery system, the product 175 simultaneously produces an insulative vacuum throughout the tubular shaft 120. A dual insulative barrier is formed by a temperature initiated transient vacuum in combination with an enhanced nucleation deposition process along the outer surface of the internal tubes (discussed infra). The nucleation sites are therefore capable of selective placement anywhere throughout the product.

In one embodiment, the distal end 128 is a needle-like probe end. In another embodiment, the distal end 128 takes the form of a blunt-tip probe end. The distal portion 128 may be integral with the tubular shaft or be removably placed in connection therewith. The interconnections of proximal connector, tubular shaft, and distal probe ends thus determines whether or not the individual parts, alone or in combination, may be reused, or disposed of. Further, the length of the distal end 28 may vary according to treatment procedure and may be any size, shape and dimension to correspond to the tissue treated.

The invention facilitates other improvements in cryotherapy, and medical devices or components associated with the treatment. The medical device of the invention allows for the circulation (cooling, delivery, and return) of liquid cryogen to a cryoprobe for the freezing of targeted tissue. The invention facilitates the eradication of tissue and can thereby decrease hospitalization time; further advantages reduce postoperative morbidities, shorten return to daily functions and work, and further lessen the overall treatment cost. These improvements to device design and application can also increase utilization of the device for the treatment of multiple disease states.

The device of the invention represents an approach in the development of cryosurgical devices by allowing for temperature induced transient vacuum insulation along the shaft of a cryoprobe or catheter; including insulating the shaft of a cryoprobe or catheter and delivery of cryogen in targeted thermal therapy. Furthermore, the device has been developed to couple the temperature initiated vacuum with that of a surface modification along the inner tubes to enable enhanced nucleation and deposition of the saturated gas on the surface of the inner tubes and create an additional layer of insulation. In one aspect, the device of the invention allows for the enhanced deposition on the outer surface of the inner tubes through modification of the tube surface, thereby creating an additional insulation barrier. In another aspect, the saturated gas filled lumen of the outer tube at ambient temperature may be either elevated or at atmospheric pressure.

The embodiments of the present invention may be modified to take the shape of any device, container, apparatus, or vessel currently used in industry. As disclosed herein, the cryoprobe device in the invention may be of any size, shape, or dimension. The device may be single use disposable or a multi-use/reusable part (and capable of being sterilized between individual patient treatments). In one embodiment, the longitudinal body extends up to about 6-8 feet or more. Any length, however, may be utilized as designed for particular therapies and treatments. Dimensions less than 12 inches, however, may also be better suited where attached tubing, removable, detachable, or disposable parts are integrated in the design. Specifically, cylindrical or alternative structural designs may be utilized in the cryogenic system for improved catheter/probe access to a tissue target. Further, any rearrangement of the tubes/lines in combination with the components of the above system may take many forms and be of any size, shape, or passageway.

In utilizing the medical device of the present invention, various methods in the industry may be employed in accordance with accepted cryogenic applications. As discussed, the embodiments of the present invention are for exemplary purposes only and not limitation. Advantageously, this device represents an important step in targeted thermal therapies. Various cryosurgical devices and procedures to apply freezing temperatures to a target tissue may be employed for use with the medical device of the present invention. The medical system disclosed herein has been developed to enable and improve some of the approaches used to target or ablate tissue. Furthermore, the medical device can couple controlled pumping of a liquid cryogen through a baffled linear heat exchanger to decrease the overall temperature of the cryogen providing a greater heat capacity of the fluid and thereby resulting in an increased cooling potential in a cryoprobe.

In one embodiment of the system, the mechanical and electrical mechanisms of the operational device is contained within a console, a shell or enclosure that allows the system to be easily transported. The enclosure may then include any mobile feature such as wheels, handles, and fixtures (or allow placement onto a cart having these features) so that the system can be transported to and from the location of treatment. Such mobility allows the system to be easily moved to and from an operating room or site of therapeutic treatment. It is also noted that the system is readily separable from the cryogen fill tanks and fill lines that initially supply the system with the liquid nitrogen or other such cryogenic fluid at the supply port 29 (As shown in FIG. 1). This improved feature eliminates the bulkiness of standard cryogenic medical devices.

As presented, the multiple embodiments of the present invention offer several improvements over standard medical devices currently used in cryogenic industry. The improved cryogenic medical devices remarkably enhance its utilization for the cooling, delivery and return of a liquid cryogen to a cryoprobe for the freezing of targeted tissue. The present invention provides cost savings and significantly reduced treatment times which further reduce expenditures in the healthcare setting. The previously unforeseen benefits have been realized and conveniently offer advantages for the treatment of multiple disease states. In addition, the improvements enable construction of the device as designed to enable easy handling, storage, and accessibility. Further uses of the system outside of the healthcare setting are foreseeable. Potential uses in the space industry, defense systems or any industry requiring rapid cooling may incorporate the cryogenic system as thus described.

As exemplified, the device may include any unitary structure, vessel, device or flask with the capacity to integrally incorporate any combination of such structures. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

What is claimed is:

1. A cryogenic system comprising:
   a container having cryogen within said container;
   one or more cryoprobes outside said container for use in cryotherapeutic procedures, said one or more cryoprobes having a distal freeze zone;
   at least one pressurized apparatus having one or more heaters arranged therein to form a pressurized cryogen, said pressurized apparatus having at least one port, and one or more control valves; at least a first portion of said pressurized apparatus submersed in the cryogen and having a first temperature, and at least a second portion of said pressurized apparatus positioned outside the cryogen and having a second temperature greater than said first temperature; wherein said pressurized apparatus generates a pressurized cryogen and is capable of generating compressed liquid cryogen, critical cryogen, pseudo-fluidic cryogen or supercritical cryogen. a cryogenic pump submersed within the cryogen which delivers the cryogen to said port of said pressurized apparatus through at least one fill line, said fill line including a valve which opens to deliver the cryogen to said port of said pressurized apparatus and closes once said pressurized apparatus is filled to a specified level;
   at least one supply line connecting said pressurized apparatus to said one or more cryoprobes and directing said pressurized cryogen through to said one or more cryoprobes to said distal freeze zone; and
   at least one return line which returns the cryogen from said distal freeze zone of said one or more cryoprobes to said container or to a subcooling chamber;
   wherein said pressurized apparatus is configured to provide controlled continuous delivery of said pressurized cryogen to said distal freeze zone of said one or more cryoprobes, said controlled continuous delivery configured for manual and remote control operation.

2. The cryogenic system of claim 1, wherein one or more manifolds direct a flow of the cryogen through to said one or more cryoprobes to target cardiac tissue, cancerous tissue, undesired tissue, or irregularities; said one or more manifolds comprising an integral assembly for directing at least a first composition or at least a second composition, alone or in combination, wherein said first composition is a liquid and said second composition is a gas.

3. The cryogenic system of claim 2, further comprising a control mechanism for varying the temperature or pressure of said first composition and said second composition, alone or in combination.

4. The cryogenic system of claim 1, wherein two or more of said pressurized apparati are configured to provide a sequential delivery of said pressurized cryogen.

5. The cryogenic system of claim 1, wherein said one or more cryoprobes comprises a condensation based vacuum insulated catheter including:
   one or more cryogenic lines internal to said condensation based vacuum insulated catheter and having an outer surface with enhanced nucleation sites;
   an outer sheath encasing said cryogenic lines and having a lumen therein filled with vapors that remain in a gaseous state at an ambient temperature and solidify upon cooling; and
   a formation of solid crystals along said outer surface of said one or more cryogenic lines and having low thermal conductivity;
   wherein said formation of solid crystals upon said enhanced nucleation sites creates an evacuated space within said lumen.

6. The cryogenic system of claim 5, wherein said evacuated space is an insulative vacuum formed from non-equilibrating phase change gas and said insulative vacuum is dependent on temperature reduction of said non-equilibrating phase change gas, said non-equilibrating phase change gas precipitating out of said lumen and solidifying upon said outer surface of said one or more cryogenic lines.

7. The cryogenic system of claim 1, wherein said one or more cryoprobes comprise a monitoring element, a sensor, or an optical imaging component, one or more thermocouples, an electrocardiogram monitor, one or more pressure transducers, and an electrophysiological sensor, individually or in any combination.

8. The cryogenic system of claim 1, wherein said one or more cryoprobes is rigid or flexible and directed to a target tissue site for a selected cryotherapeutic procedure, said one or more cryoprobes capable of being activated individually or collectively to produce a desired temperature or freeze duration.

9. The cryogenic system of claim 1, wherein said first portion and said second portion of said pressurized apparatus are individual interconnected pressurization chambers comprising a first pressurization chamber inside said container of the cryogen and a second pressurization chamber outside of the cryogen.

10. The cryogenic system of claim 1, further comprising a baffled linear heat exchanger.

11. The cryogenic system of claim 10, wherein said baffled linear heat exchanger is surrounded by a subcooling chamber or a cryogen reservoir.

12. The cryogenic system of claim 1, wherein the cryogen is nitrogen and said pressurized apparatus forms supercritical nitrogen.

13. The cryogenic system of claim 1, wherein said one or more cryoprobes comprises:
   an outer sheath forming a longitudinal body having a proximal end and a closed distal end such that a lumen is created therebetween;
   two or more cryogenic lines positioned in parallel or coaxially within said lumen and having an open-ended configuration at said closed distal end of said longitudinal body, said two or more cryogenic lines interconnected with said supply lines and said return lines such that delivery of said pressurized cryogen to said closed distal end of said longitudinal body creates said distal freeze zone; and
   a vacuum created in said lumen around and between said cryogenic lines;
   wherein said distal freeze zone is a linear configuration, a curved linear configuration, or a spot freeze zone.

14. The cryogenic system of claim 13, wherein said open-ended configuration of said two or more cryogenic lines is linked to form a unitary structure at said closed distal end.

15. The cryogenic system of claim 14, wherein said unitary structure forms a closed loop tip, a closed loop coil with or without an internal heat exchanger, an inflatable cryogenic element, or a configuration which creates an isolated freeze zone.

16. The cryogenic system of claim 13, wherein said distal freeze zone is an inflatable cryogenic element in the configuration of a balloon.

17. A method of delivering cryogen to a cryoprobe utilizing the cryogenic system of claim 1, said method comprising the steps of:
- filling a first portion of said one or more pressurized apparati;
- activating said one or more pressurized apparati to form a supercritical cryogen; and
- controllably directing said pressurized cryogen to said one or more cryoprobes through said one or more supply lines and from said instrument through said one or more return lines;

wherein said step of activating said one or more pressurized apparati includes a step of pressurizing each of said pressurized apparati and releasing said pressurized cryogen in a controlled continual sequence.

18. A cryogenic system comprising:
- a cryogen reservoir filled with a cryogen;
- one or more cryoprobes outside said cryogen reservoir, said one or more cryoprobes having a distal freeze zone;
- at least a first pressurization chamber and a second pressurization chamber linked together, each comprising: one or more heaters arranged therein to form a pressurized cryogen, one or more ports, and one or more control valves;
- a cryogenic pump submersed within the cryogen which delivers the cryogen to at least one of said one or more ports;
- at least one supply line connecting said first pressurization chamber to said one or more cryoprobes and directing said pressurized cryogen through to said distal freeze zone; and
- at least one return line which returns the cryogen from said distal freeze zone of said one or more cryoprobes to said cryogen reservoir;

wherein said first pressurization chamber is submersed in said cryogen reservoir and having a first temperature, and said second of said pressurization chambers is positioned outside the cryogen and having a second ambient temperature greater than said first temperature to generate a supercritical cryogen.

* * * * *